(12) United States Patent
Brown et al.

(10) Patent No.: US 7,570,740 B2
(45) Date of Patent: Aug. 4, 2009

(54) RADIOTHERAPY APPARATUS AND PARTS THEREOF

(75) Inventors: Kevin Brown, Horsham (GB); Paul Boxall, Maidenbower (GB)

(73) Assignee: Elekta AB (publ), Stockholm (SE)

( * ) Notice: Subject to any disclaimer, the term of this patent is extended or adjusted under 35 U.S.C. 154(b) by 102 days.

(21) Appl. No.: 11/925,339

(22) Filed: Oct. 26, 2007

(65) Prior Publication Data

US 2009/0110150 A1    Apr. 30, 2009

(51) Int. Cl.
*H05G 1/38* (2006.01)
(52) U.S. Cl. .................. 378/108; 378/65; 378/117
(58) Field of Classification Search ............... 378/64, 378/65, 97, 108, 114, 117; 600/427; 250/492.1–492.3
See application file for complete search history.

(56) References Cited

U.S. PATENT DOCUMENTS

| | | | | |
|---|---|---|---|---|
| 4,047,043 | A * | 9/1977 | Meyer | 378/97 |
| 5,635,714 | A * | 6/1997 | Nablo et al. | 250/305 |
| 6,240,162 | B1 * | 5/2001 | Hernandez-Guerra et al. | 378/65 |
| 7,286,641 | B2 * | 10/2007 | Brendler et al. | 378/110 |
| 7,307,264 | B2 * | 12/2007 | Brusasco et al. | 250/492.22 |
| 2006/0088655 | A1 * | 4/2006 | Collins et al. | 427/8 |
| 2008/0144772 | A1 * | 6/2008 | Yi et al. | 378/65 |

* cited by examiner

*Primary Examiner*—Edward J Glick
*Assistant Examiner*—Thomas R Artman
(74) *Attorney, Agent, or Firm*—Lahive & Cockfield, LLP; Anthony A. Laurentano

(57) ABSTRACT

The detected positioning error in a geometry item of a radiotherapy apparatus is generally passed to a transfer function for the system, which outputs a signal that dictates the radiation output. If the detected error is within certain limits then the radiation is permitted whereas outside those limits it is not permitted; this corresponds to a transfer function that is a simple two step function. We propose a transfer function having a result that is (a) substantially zero outside a preset error tolerance, (b) has a maximum result at a point within that tolerance, and (c) has a result that is between zero and that maximum over a range of error values that lie between (i) the error value corresponding to the maximum output and (ii) the preset error tolerance. This means that if an error grows towards (but does not exceed) the error tolerance, the output of the radiation source will reduce and allow time for the geometry item to correct its position.

11 Claims, 4 Drawing Sheets

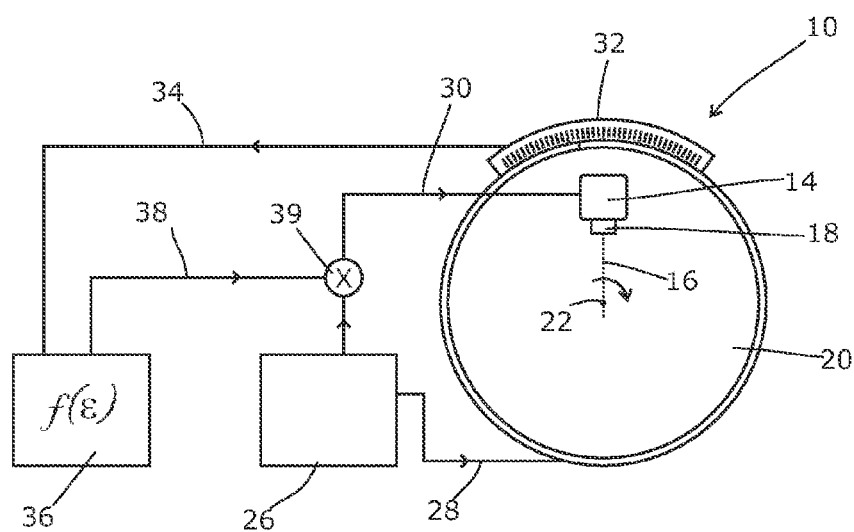
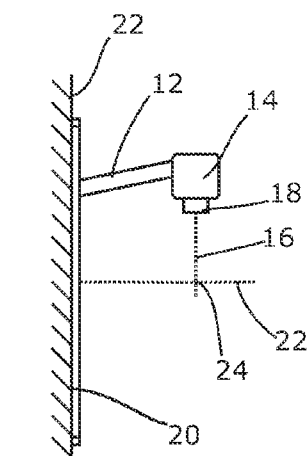
Fig 1a        Fig 1b
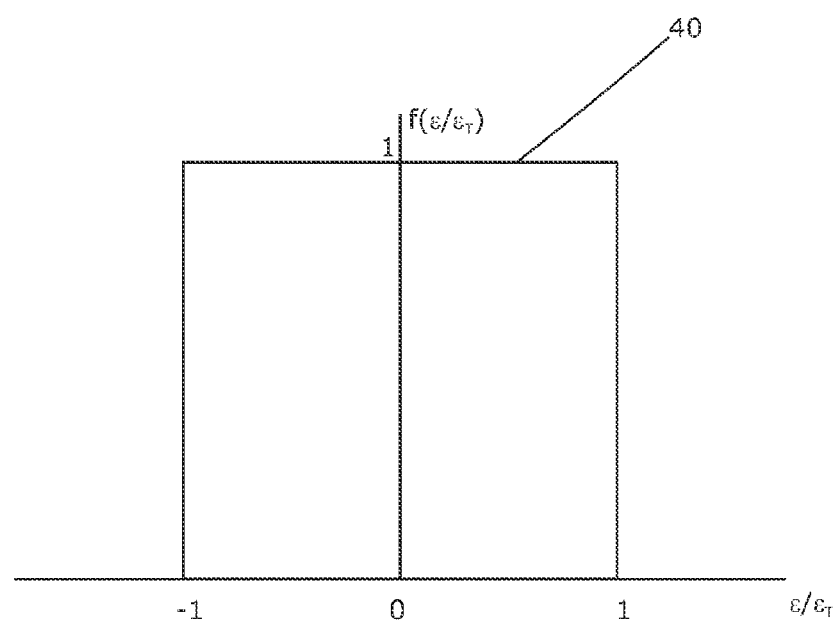
Fig 2

RADIOTHERAPY APPARATUS AND PARTS THEREOF

FIELD OF THE INVENTION

The present invention relates to radiotherapeutic apparatus, and to improvements in the transfer functions that are used in controlling them.

BACKGROUND ART

Radiotherapeutic apparatus generally comprises a radiation source which produces a beam of therapeutic radiation, i.e. radiation at a suitably high energy level to cause damage to tissue through which it passes. The beam is then collimated and directed towards a patient. This collimation of the beam seeks to limit its lateral extent so that it selectively irradiates a tumour within the patient and thereby causes harm to the tumour.

Generally, the radiation source is supported on a gantry extending from a mount which is rotated during irradiation so as to direct the beam towards the patient from a variety of directions. This means that the portion of healthy tissue through which the beam passes in order to irradiate the tumour varies with time, and the total radiation dose delivered to any particular volume of healthy tissue is thereby minimised. As the radiation source rotates around the patient, the collimation of the beam may be changed, for example to reflect the changing projected shape of the tumour (in a conformal arc-type therapy), or to lay down differing dose distributions (in intensity modulated radiotherapy applications). In the latter example, the dose rate or intensity of the beam may be adjusted as the treatment progresses in order to create a three-dimensional prescription that is individual to the patient concerned. Thus, as the treatment progresses, the gantry angle, the collimation, and the beam intensity may all be varying dynamically. These must obviously be monitored for error.

Where an error beyond an acceptable threshold is detected, the radiation source is deactivated in order to prevent harm being caused to the patient. A certain threshold of error must be permitted, simply because there will inevitably be some degree of lag, inertia and other measurement error in the system, and hence a zero threshold would have the potential to stop all treatment or to make treatment so slow that it becomes inefficient.

SUMMARY OF THE INVENTION

In practice, this threshold can be achieved by defining a "transfer function" for the system, in which the radiation output is dictated by the detected total error; if that detected error is within certain limits then the radiation is permitted, whereas outside those limits it is not permitted. The corresponding transfer function is shown in FIG. 1, and is a simple two step function. Outside a certain error threshold, the radiation output is zero. Where the error is within that threshold, the radiation output is on.

If we express the error $\epsilon$ as a proportion of the total permitted error $\epsilon_T$, and the output $f(\epsilon/\epsilon_T)$ as 0 for off and 1 for on, the function is therefore such that for $\epsilon/\epsilon_T < -1$ then $f(\epsilon/\epsilon_T)=0$, for $-1 < \epsilon/\epsilon_T < 1$ then $f(\epsilon/\epsilon_T)=1$, and for $\epsilon/\epsilon_T > 1$ then $f(\epsilon/\epsilon_T)=0$. This produces the graph shown in FIG. 1.

We have observed that the sudden step change in the transfer function at $\epsilon/\epsilon_T = \pm 1$ is undesirable, in that it leads to a sudden cessation in the treatment delivery. This can lead to a jerky or stuttering delivery that will be unnecessarily lengthy, mechanically unsympathetic, and disconcerting for the patient.

We therefore propose a transfer function having a result that is (a) substantially zero outside a preset error tolerance, (b) has a maximum result at a point within that tolerance, and (c) has a result that is between zero and that maximum over a range of error values that lie between (i) the error value corresponding to the maximum output and (ii) the preset error tolerance.

This would mean that if an error grew towards (but did not exceed) the error tolerance, the output of the radiation source would reduce. This would seem counter-intuitive; the apparatus is within its error tolerance and therefore operating acceptably, but we are proposing that the treatment rate be reduced thereby undesirably lengthening the treatment time. However, the growing error can be taken to indicate that at least one geometry item is not keeping up with the dose that is being delivered. Accordingly, the reduction in dose rate allows time for that geometry item to correct its position—in effect, the slowing of the delivery of radiation reduces the demand on the geometry item to move as quickly. If therefore the error has arisen because the geometry item is not able to move quickly enough for some reason, the progress of the treatment is slowed to allow for this.

The alternative, as embodied in known transfer functions, is to wait until the error has grown still further and then halt treatment completely. This does permit the geometry item to catch up to its correct location, but results in both a sudden stop and a potentially greater lengthening of the treatment time (if treatment continues). There is then a sudden start when the error is reduced, followed by another sudden stop when the error grows again. A soft transfer function of the type defined above will be permitted to settle at a reduced dose rate that is compatible with the current performance ability of the geometry item concerned.

This can be embodied in a radiotherapeutic apparatus comprising a source of radiation able to emit a beam of radiation, and at least one geometry item arranged to control the geometry of the beam, the dose rate of the source being variable according to such a transfer function that acts on a detected error to produce a dose rate command signal.

The maximum result of the transfer function preferably corresponds to a zero error, and can be a plateau of the function rather than a localised peak. Generally, we prefer the result of the transfer function to fall smoothly from the maximum to zero with few or no sudden changes. This reduces the very high frequency components of the function that are associated with step changes (or the like), and contributes towards a smooth operation of the apparatus. A function with a plateau region could also be combined with a data logger to record when the output departed from that plateau; if this were common then it could be used as a warning that maintenance or rectification action was needed.

Alternatively, the result of the transfer function can descend from the maximum to zero in one or more discrete steps, or it can fall linearly from the maximum to zero.

The geometry item can be one that controls the path of the beam, or it can be one that controls the cross-sectional shape of the beam. These correspond (for example) to the gantry arm on which the source is located and the leaves of a multi-leaf collimator, respectively. It will be apparent that transfer functions can be provided for each such geometry item, or the detected error from multiple geometry items can be combined and supplied to a single transfer function.

BRIEF DESCRIPTION OF THE DRAWINGS

An embodiment of the present invention will now be described by way of example, with reference to the accompanying figures in which;

FIGS. 1a and 1b show in schematic form a radiotherapy apparatus capable of embodying the present invention;

FIG. 2 shows a transfer function corresponding to known systems;

DETAILED DESCRIPTION OF THE EMBODIMENTS

Figure 3:
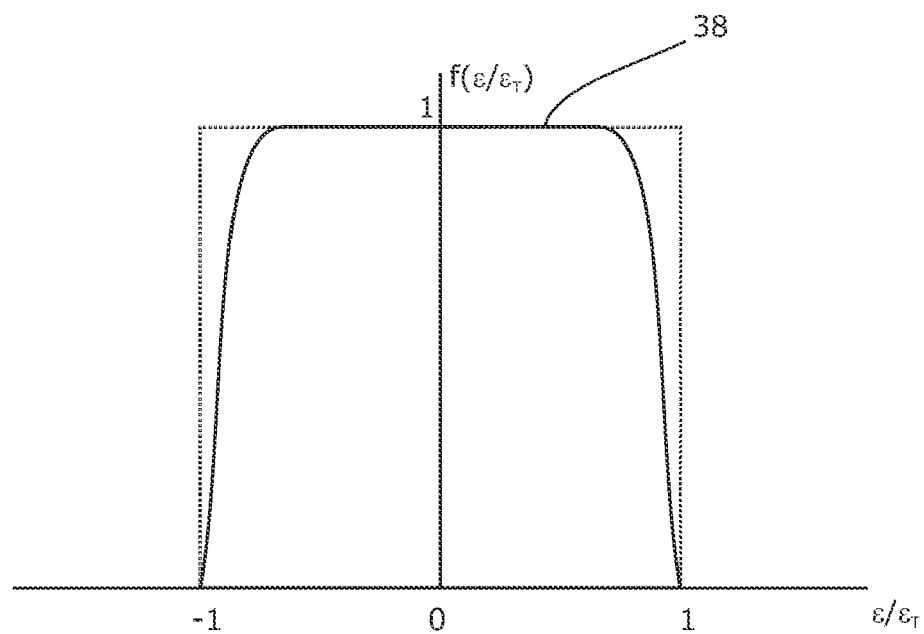
FIGS. 3 to 8 show alternative transfer functions according to the present invention.

FIGS. 1a and 1b show a radiotherapy apparatus. A gantry arm 12 supports a radiation head 14 which is adapted to emit a beam of radiation 16. Before the beam 16 leaves the radiation head 14 it is collimated by (in this case) a multi-leaf collimator 18. The gantry arm 12 extends from a rotatable support 20 which is generally mounted in a wall 22, behind which the necessary mechanics are provided to support the gantry arm 12, deliver services such as electrical power, data signals and cooling water, and to enable the rotation of the support 20 about a central axis 22.

The gantry arm 12 is displaced from that central axis 22, and the radiation head 14 is aligned so that the beam 16 is directed back to towards that axis 22. The beam 16 and the axis 22 are coincident at a point 24 known as the iso-centre. Thus, as the support 20 rotates around the axis 22, the isocentre 24 remains within the beam 16 at all times (subject to the beam shape imposed by the multi-leaf collimator 18). Generally, therefore, the patient will be located on a suitable patient support so that the tumour is positioned at the isocentre 24. During treatment, the apparatus is control by a treatment controlled computer 26, which has suitable data lines 28 to control rotation of the support 20 and a data line 30 to control the intensity of the source 14 and the leaves of the multi-leaf collimator 18. All three factors may be varied during treatment in a dynamic manner.

FIG. 1a also shows (schematically) a position monitoring system 32 for the support 20 which reports back on the current actual rotational position of the support 20. A similar system can be provided for the position of the leaves of the multi-leaf collimator 18. This reports back by a data line 34 to a treatment monitoring computer 36, which determines any error in the position that is reported and applies a transfer function to it, the result of which is output by a data line 38. That output is then applied to the output 30 of the treatment control computer 26, in this case by way of a multiplication step 39. Thus, when the output 36 of the treatment monitoring computer is zero, this will command a zero intensity from the radiation source 14 and, in effect, the temporary cessation of treatment. An output of 1 from the treatment monitoring computer 36 will allow treatment to continue, and outputs of between 1 and zero will allow treatment to continue at a reduced dose rate.

Of course, in this specific instance the functions of the treatment control computer 26 and the treatment monitoring computer 36 may be combined into a single computing function that takes account of all relevant factors in order to determine a treatment rate. However, for clarity of description we have shown the two functions as being separate in FIG. 1a.

It would be appreciated that, as a result of the programming of the treatment control computer 26 to servo the different factors involved in treatment to each other, a commanded reduction in the dose rate will result in instructions to the gantry rotation and the multi-leaf collimator to slow down the rate at which these move.

FIG. 2, described above, shows the transfer function that is in effect applied by a conventional system. A total permitted error $\epsilon_T$ is determined in advance and corresponds to the maximum permissible error allowed in the system. For measured errors $\epsilon$ greater than $\epsilon_T$, either positive or negative, the output of the transfer function $f(\epsilon/\epsilon_T)$ is zero. Where $\epsilon/\epsilon_T$ is between −1 and 1, this indicates that the total error is within the prescribed tolerances and the output of the transfer function is 1, allowing treatment to continue.

This has the side-effects noted above, and we therefore propose the softened transfer function shown in FIG. 3. This has a plateau region 38 centered on $\epsilon/\epsilon_T$ and continuing up to $\epsilon/\epsilon_T \approx \pm 0.6$ or 0.7. At this point, the output of the function begins to smoothly tail off towards zero at $\epsilon/\epsilon_T = \pm 1$. Thus, provided the total error remains small, the apparatus can continue unaffected whilst in the plateau region. However, as the error begins to grow the dose rate is reduced at an earlier stage, but is not cut off completely. Instead, the dose rate reduces and therefore the treatment control computer 26 responds by commanding slower movements of the gantry arm 12 and the leaves of the multi-leaf collimator 18, in other words slowing the total treatment. Of course, the error has arisen because one or more geometry items have been unable to keep up with the dose being delivered and have therefore fallen back; this slowing of the dose rate will therefore reduce the commanded rate of movement of geometry items down to one which is actually being achieved in practice. As a result, where errors are arising because geometry items are unable, in this instance, to move at the expected maximum speed, the soft transfer function succeeds in slowing the overall treatment down to the actual achievable speed of the geometry items without departing from the prescribed error tolerances and without resorting to a jerky and interrupted treatment style. Of course, given that the sudden jerking stops of the gantry arm will be apparent to the patient, such a jerky style of treatment is extremely disconcerting since it is clear to the patient that something is not right.

Figure 4:
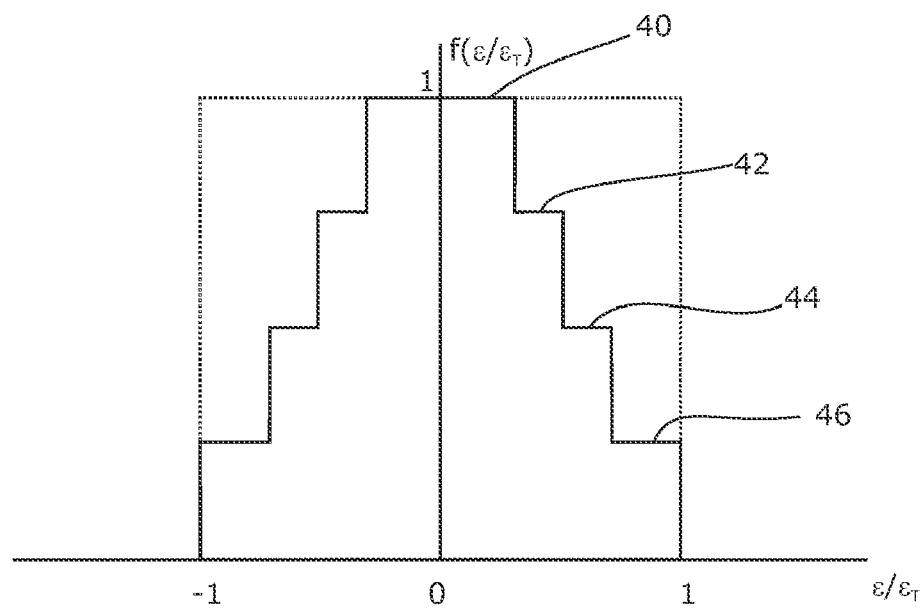

This transfer function needs to be embodied in software of the treatment monitoring computer 36. It may be that the smoothly varying function of FIG. 3 will be difficult to embody in practice. Accordingly, as an alternative, the transfer function of FIG. 4 could be applied. This retains a central plateau 40 albeit (in this instance) that is significantly reduced in width, but the output of the function is reduced in three steps 42, 44, 46, each of 25%, until at $\epsilon/\epsilon_T = 1$ the output of the transfer function equals zero. As illustrated in FIG. 4, each step is equal as the function descends towards zero, but this need not be the case. Steps could be varied in width so as to extend the central plateau region 40 at the expense of the faster reduction as the error increases, and/or the sizes of the steps could be varied, for example by making the initial step slightly less.

Figure 5:
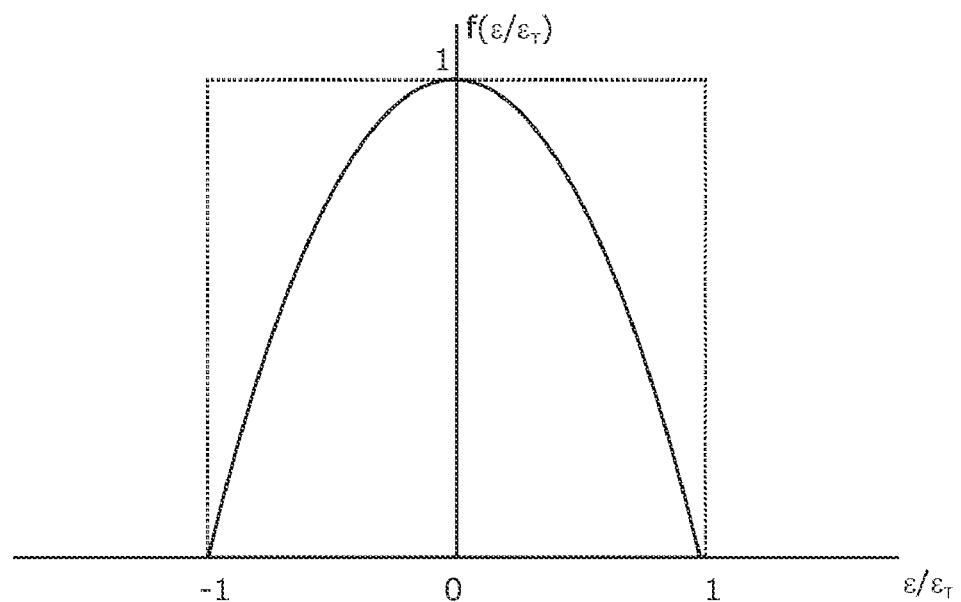

FIG. 5 shows an alternative transfer function which will be straight forward to embody as it is a simple parabolic curve that can be represented by a quadratic function such as $f(\epsilon/\epsilon_T) = (1+\epsilon/\epsilon_T)(1-\epsilon/\epsilon_T)$. Although this lacks the central plateau region and will therefore start to cut down the dose rate immediately upon any error is detected (however small) it does have the advantage of computational simplicity, requiring only a simple quadratic function (above) together with a step of zeroing any negative result.

Figure 6:
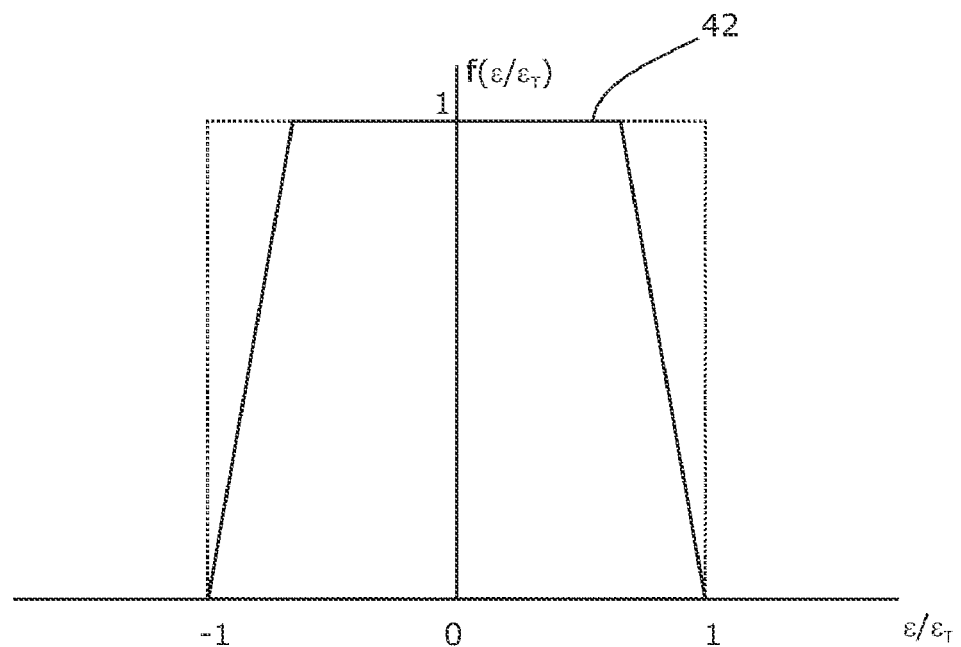

FIG. 6 shows an alternative form of transfer function that is also computationally straight-forward but retains a central plateau 42. This plateau extends approximately as far as $\epsilon/\epsilon T=\pm 0.7$, at which point a simple linear function takes over to reduce the outgoing function to zero as $\epsilon/\epsilon_T=\pm 1$.

Figure 7:
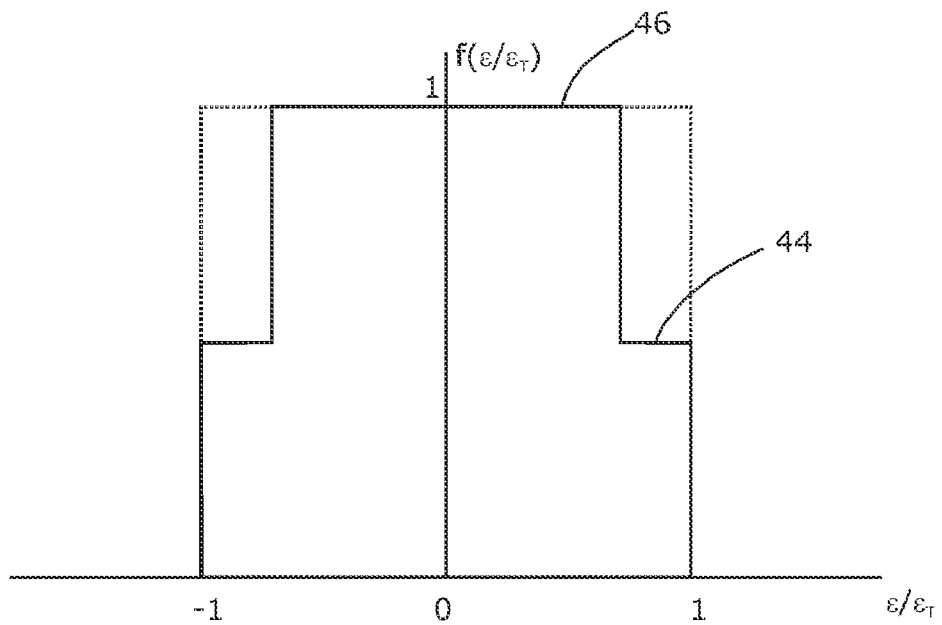

Finally, FIG. 7 shows probably the simplest form of function in which there is a single step 44 down from a central plateau 46 before the result of the transfer function drops to zero outside the prescribed error tolerances. This therefore provides a "catch up" zone outside the central plateau.

Figure 8:
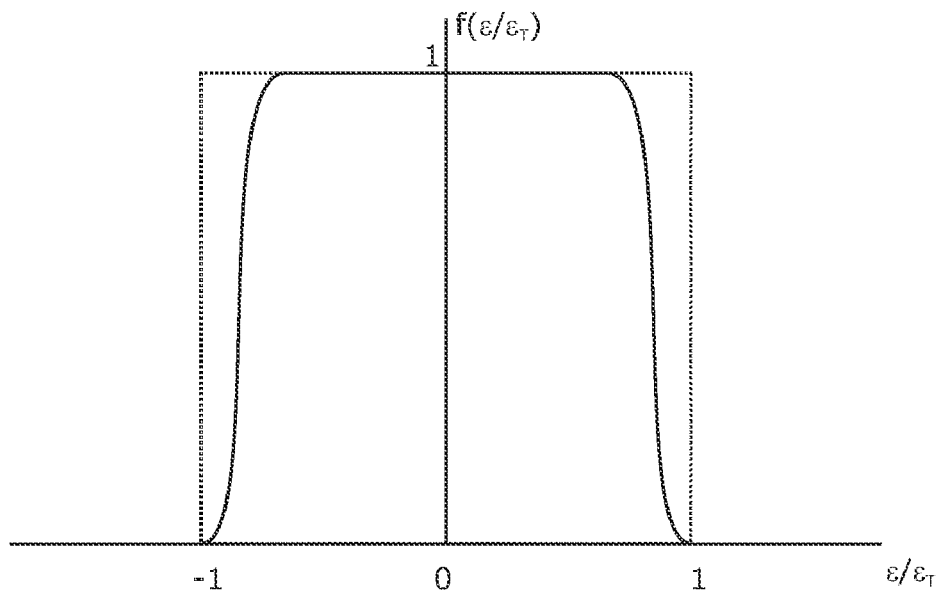

FIG. 8 shows a further alternative form of transfer function, which is generally similar to that illustrated in FIG. 3 except that as $\epsilon_T$ approaches $\pm 1$, the output of a function smoothly approaches zero rather than suddenly changing from a downward slope to a flat output. This function successfully removes all high frequency components from the function's output since smooth transitions are present at all points. Generally, we prefer to avoid sharp transitions in the function as these correspond to sudden and jerky movements.

It will of course be understood that many variations may be made to the above-described embodiment without departing from the scope of the present invention.

The invention claimed is:

1. A radiotherapeutic apparatus comprising a source of radiation able to emit a beam of radiation, and at least one geometry item arranged to control the geometry of the beam, the dose rate of the source being variable according to a transfer function that acts on a detected error to produce a dose rate command signal, the transfer function having a result that is (a) substantially zero outside a preset error tolerance, (b) has a maximum result at a point within that tolerance, and (c) has a result that is between zero and that maximum over a range of error values that lie between (i) the error value corresponding to the maximum output and (ii) the preset error tolerance.

2. A radiotherapeutic apparatus according to claim 1 in which the maximum result of the transfer function corresponds to a zero error.

3. A radiotherapeutic apparatus according to claim 1 in which the transfer function has a plateau around the maximum result.

4. A radiotherapeutic apparatus according to claim 3 comprising means for logging instances where the output of the function departed from the plateau region.

5. A radiotherapeutic apparatus according to claim 1 in which the result of the transfer function falls smoothly from the maximum to zero.

6. A radiotherapeutic apparatus according to claim 1 in which the result of the transfer function descends from the maximum to zero in at least one discrete step.

7. A radiotherapeutic apparatus according to claim 1 in which the result of the transfer function falls linearly from the maximum to zero.

8. A radiotherapeutic apparatus according to claim 1 in which the geometry item controls the path of the beam.

9. A radiotherapeutic apparatus according to claim 8 in which the geometry item is a gantry arm on which the source is located.

10. A radiotherapeutic apparatus according to claim 1 in which the geometry item controls the cross-sectional shape of the beam.

11. A radiotherapeutic apparatus according to claim 10 in which the geometry item is at least one leaf of an multi-leaf collimator.

* * * * *